(12) United States Patent
Hayashida et al.

(10) Patent No.: US 11,317,960 B2
(45) Date of Patent: May 3, 2022

(54) ELECTRIC POWER SOURCE DEVICE, HIGH-FREQUENCY TREATMENT SYSTEM, AND ACTUATING METHOD OF ELECTRIC POWER SOURCE

(71) Applicant: OLYMPUS CORPORATION, Tokyo (JP)

(72) Inventors: Tsuyoshi Hayashida, Hachioji (JP); Yoshitaka Honda, Hachioji (JP); Norihiko Hareyama, Hino (JP); Ko Kawashima, Musashino (JP); Kenji Matsuki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 353 days.

(21) Appl. No.: 16/557,447

(22) Filed: Aug. 30, 2019

(65) Prior Publication Data

US 2020/0000507 A1 Jan. 2, 2020

Related U.S. Application Data

(63) Continuation of application No. PCT/JP2017/008334, filed on Mar. 2, 2017.

(51) Int. Cl.
*A61B 18/12* (2006.01)
*A61B 18/14* (2006.01)
*A61B 18/00* (2006.01)

(52) U.S. Cl.
CPC ...... *A61B 18/1206* (2013.01); *A61B 18/1445* (2013.01); *A61B 2018/00404* (2013.01); *A61B 2018/00702* (2013.01); *A61B 2018/00767* (2013.01); *A61B 2018/00779* (2013.01); *A61B 2018/00827* (2013.01);

(Continued)

(58) Field of Classification Search
CPC .................. A61B 18/1206; A61B 18/1445
See application file for complete search history.

(56) References Cited

U.S. PATENT DOCUMENTS

| 6,033,399 A | 3/2000 | Gines |
| 2004/0193148 A1 | 9/2004 | Wham et al. |

(Continued)

FOREIGN PATENT DOCUMENTS

| JP | H10-286261 A | 10/1998 |
| JP | 2001-269353 A | 10/2001 |

(Continued)

OTHER PUBLICATIONS

Sep. 12, 2019 English Translation of International Preliminary Report on Patentability issued in PCT/JP2017/008334.

(Continued)

*Primary Examiner* — Michael F Peffley
*Assistant Examiner* — Samantha M Good
(74) *Attorney, Agent, or Firm* — Oliff PLC

(57) ABSTRACT

A processor of an electric power source device exercises control over a power output before a control switching time point based on a value related to initial impedance, and determines the control switching time point upon detecting that a value related to impedance of a living tissue is at a minimum. The processor sets a set electric-power value of the power output based on a parameter related to controlling the power output before the control switching time point, and performs constant-electric-power control by controlling the power output using the electric-power value at and after the control switching time point.

14 Claims, 10 Drawing Sheets

(52) U.S. Cl.
CPC .............. *A61B 2018/00875* (2013.01); *A61B 2018/00886* (2013.01); *A61B 2018/00892* (2013.01)

(56) References Cited

U.S. PATENT DOCUMENTS

| | | |
|---|---|---|
| 2007/0282320 A1 | 12/2007 | Buysse et al. |
| 2008/0082095 A1 | 4/2008 | Shores et al. |
| 2010/0094276 A1 | 4/2010 | Kabaya et al. |
| 2011/0028963 A1 | 2/2011 | Gilbert |
| 2012/0283733 A1 | 11/2012 | Schall et al. |
| 2016/0374746 A1 | 12/2016 | Takami et al. |
| 2017/0079707 A1 | 3/2017 | Hareyama et al. |

FOREIGN PATENT DOCUMENTS

| | | |
|---|---|---|
| JP | 2005-40616 A | 2/2005 |
| JP | 2007-319684 A | 12/2007 |
| JP | 2011-31048 A | 2/2011 |
| JP | 2012-232142 A | 11/2012 |
| JP | 2014-100583 A | 6/2014 |
| WO | 2010/044354 A1 | 4/2010 |
| WO | 2016/067800 A1 | 5/2016 |
| WO | 2016/076365 A1 | 5/2016 |
| WO | 2017/018023 A1 | 2/2017 |
| WO | 2017/018205 A1 | 2/2017 |

OTHER PUBLICATIONS

May 16, 2017 International Search Report issued in International Patent Application No. PCT/JP2017/008334.

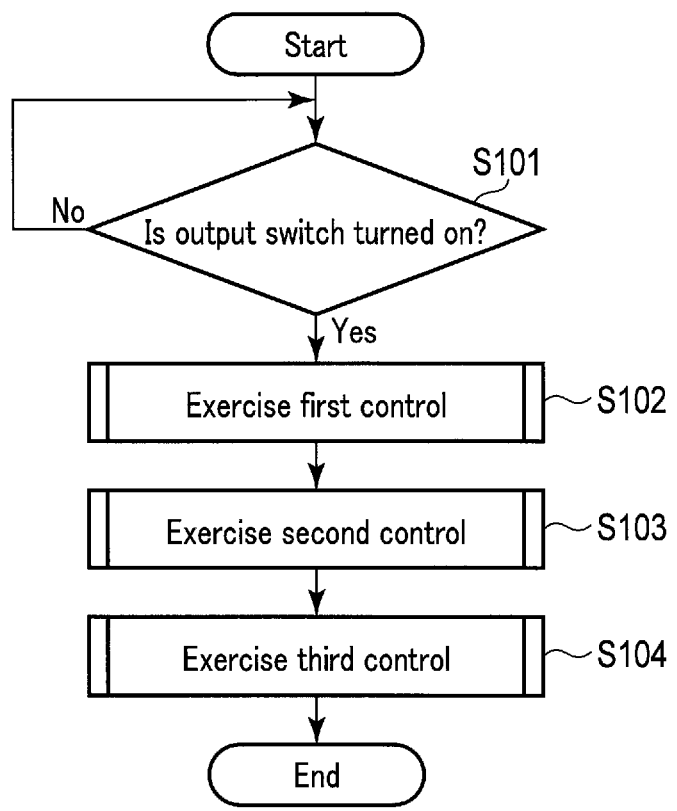
F I G. 3

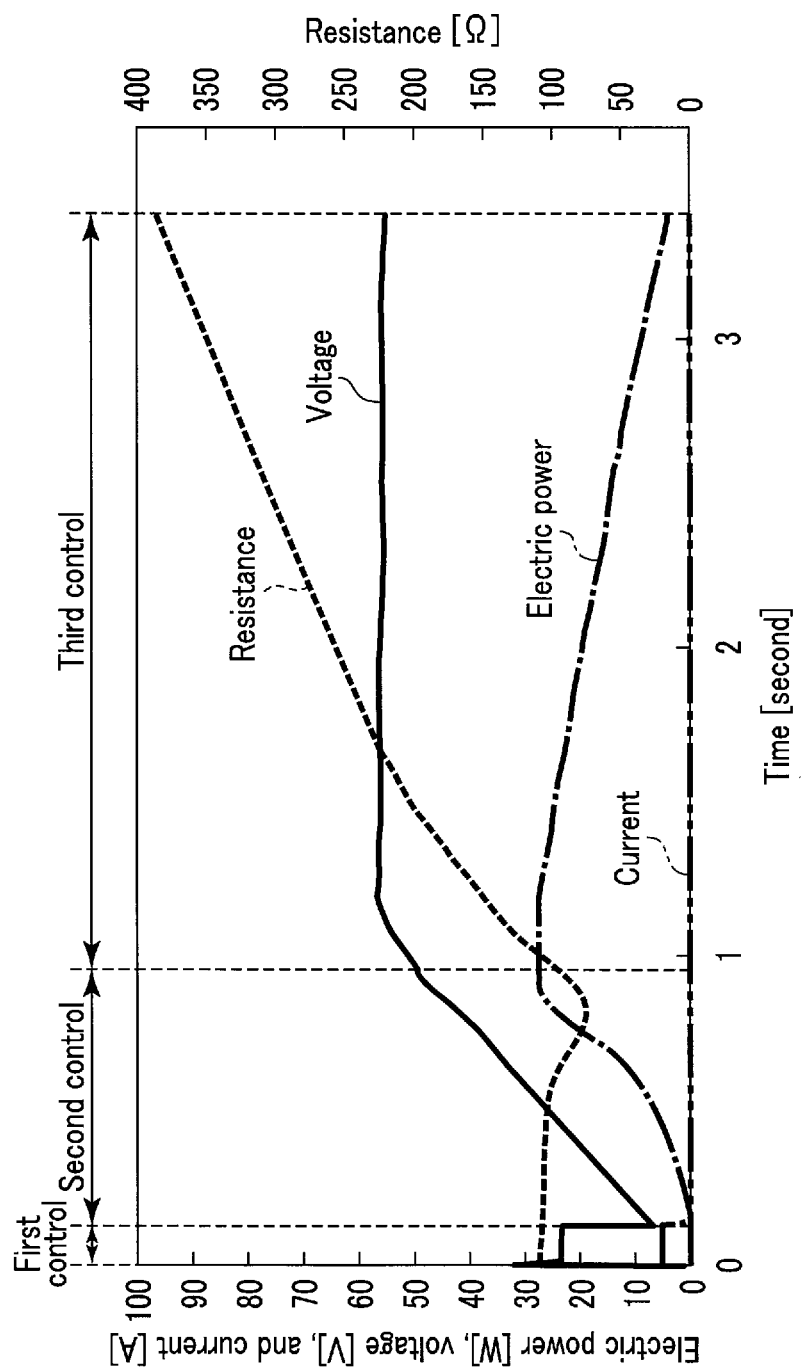
F I G. 4

| Initial resistance value R0 / Duration Dt | R0_1 | R0_2 | R0_3 | R0_4 |
|---|---|---|---|---|
| Dt_1 | a | b | c | d |
| Dt_2 | e | f | g | h |
| Dt_3 | i | j | k | l |

FIG. 8

| Initial resistance value R0 | R0_1 | R0_2 | R0_3 | R0_4 |
|---|---|---|---|---|
| Set electric-power value Wset | a | b | c | d |

FIG. 9

| Duration Dt | Dt_1 | Dt_2 | Dt_3 | Dt_4 |
|---|---|---|---|---|
| Set electric-power value Wset | a | b | c | d |

FIG. 10

| Duration Dt \ Initial resistance value R0 | R0_1 | R0_2 | R0_3 | R0_4 |
|---|---|---|---|---|
| Dt_1 | Wset_a, Vset_a, Radd_a, Tmin_a, | Wset_b, Vset_b, Radd_b, Tmin_b, | Wset_c, Vset_c, Radd_c, Tmin_c, | Wset_d, Vset_d, Radd_d, Tmin_d, |
| Dt_2 | Wset_e, Vset_e, Radd_e, Tmin_e, | Wset_f, Vset_f, Radd_f, Tmin_f, | Wset_g, Vset_g, Radd_g, Tmin_g, | Wset_h, Vset_h, Radd_h, Tmin_h, |
| Dt_3 | Wset_i, Vset_i, Radd_i, Tmin_i, | Wset_j, Vset_j, Radd_j, Tmin_j, | Wset_k, Vset_k, Radd_k, Tmin_k, | Wset_l, Vset_l, Radd_l, Tmin_l, |

FIG. 11

ELECTRIC POWER SOURCE DEVICE, HIGH-FREQUENCY TREATMENT SYSTEM, AND ACTUATING METHOD OF ELECTRIC POWER SOURCE

CROSS-REFERENCE TO RELATED APPLICATIONS

This is a Continuation Application of PCT Application No. PCT/JP2017/008334, filed Mar. 2, 2017, the entire contents of which are incorporated herein by reference.

BACKGROUND

1. Field of the Invention

The present embodiments relate to an electric power source device, a high-frequency treatment system, and an actuating method of an electric power source device.

2. Description of the Related Art

A high-frequency treatment system in which a pair of grasping members grasp living tissue which is a treatment target, to treat living tissue by supply of high-frequency electric power to the living tissue, is generally known. In such a system as described, living tissue grasped by grasping members is heated when a high-frequency current flows through the living tissue. A high-frequency treatment system like this is used for sealing a blood vessel, for example. In a high-frequency treatment system, it is required to appropriately adjust an output voltage and an output current in order to improve accuracy and efficiency of treatment.

SUMMARY

According to one aspect, an electric power source device is configured to control an output to a treatment instrument that treats living tissue with a high-frequency current. The electric power source device includes at least one processor configured to: acquire a value related to initial impedance of the living tissue; exercise control over the output before a control switching time point based on the value related to the initial impedance; determine the control switching time point when it is detected that a value related to impedance of the living tissue becomes a minimum, and control the output until the control switching time point; set a set electric-power value of the output based on a parameter related to the control over the output before the control switching time point, and exercise constant-electric-power control over the output using the set electric-power value at and after the control switching time point; and in a case where by the constant-electric-power control, a voltage value of the output is made equal to or higher than a set voltage value that is set based on at least one of the initial impedance, an output voltage value at the control switching time point, and an output time before the control switching time point, exercise constant-voltage control over the output using the set voltage value.

According to another aspect, an actuating method of an electric power source device, which is configured to control an output to a treatment instrument that treats living tissue with a high-frequency current, includes: acquiring a value related to initial impedance of the living tissue; exercising control over the output before a control switching time point based on the value related to the initial impedance; determining the control switching time point when it is detected that a value related to impedance of the living tissue becomes a minimum, and controlling the output until the control switching time point; setting a set electric-power value of the output based on a parameter related to the control over the output before the control switching time point, and exercising constant-electric-power control over the output using the set electric-power value at and after the control switching time point; and in a case where by the constant-electric-power control, a voltage value of the output is made equal to or higher than a set voltage value that is set based on at least one of the initial impedance, an output voltage value at the control switching time point, and an output time before the control switching time point, exercising constant-voltage control over the output using the set voltage value.

Advantages of the embodiments will be set forth in the description which follows, and in part will be obvious from the description, or may be learned by practice. The advantages may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments, and together with the general description given above and the detailed description of the embodiments given below, serve to explain the principles of the embodiments.

FIG. 3 is a flow chart showing an example of operations of the high-frequency treatment system according to the embodiment, FIG. 4 is a view showing an example of changes in electric power, a voltage, a current, and a resistance with time in the high-frequency treatment system according to the embodiment, FIG. 8 is a view showing an example of a table which includes a relationship among an initial resistance value, a duration, and a set electric-power value, and which is used in the high-frequency treatment system according to the embodiment, FIG. 9 is a view showing an example of a table which includes a relationship between an initial resistance value and a set electric-power value, and which is used in the high-frequency treatment system according to the embodiment, FIG. 10 is a view showing an example of a table which includes a relationship between a duration and a set electric-power value, and which is used in the high-frequency treatment system according to the embodiment, FIG. 11 is a view showing an example of a table which includes relationships of a set electric-power value, a set voltage value, an added resistance value, and a minimum output time, relative to an initial resistance value and a duration, and which is used in the high-frequency treatment system according to the embodiment.

DETAILED DESCRIPTION

[Configuration of High-frequency Treatment System]

Figure 1:
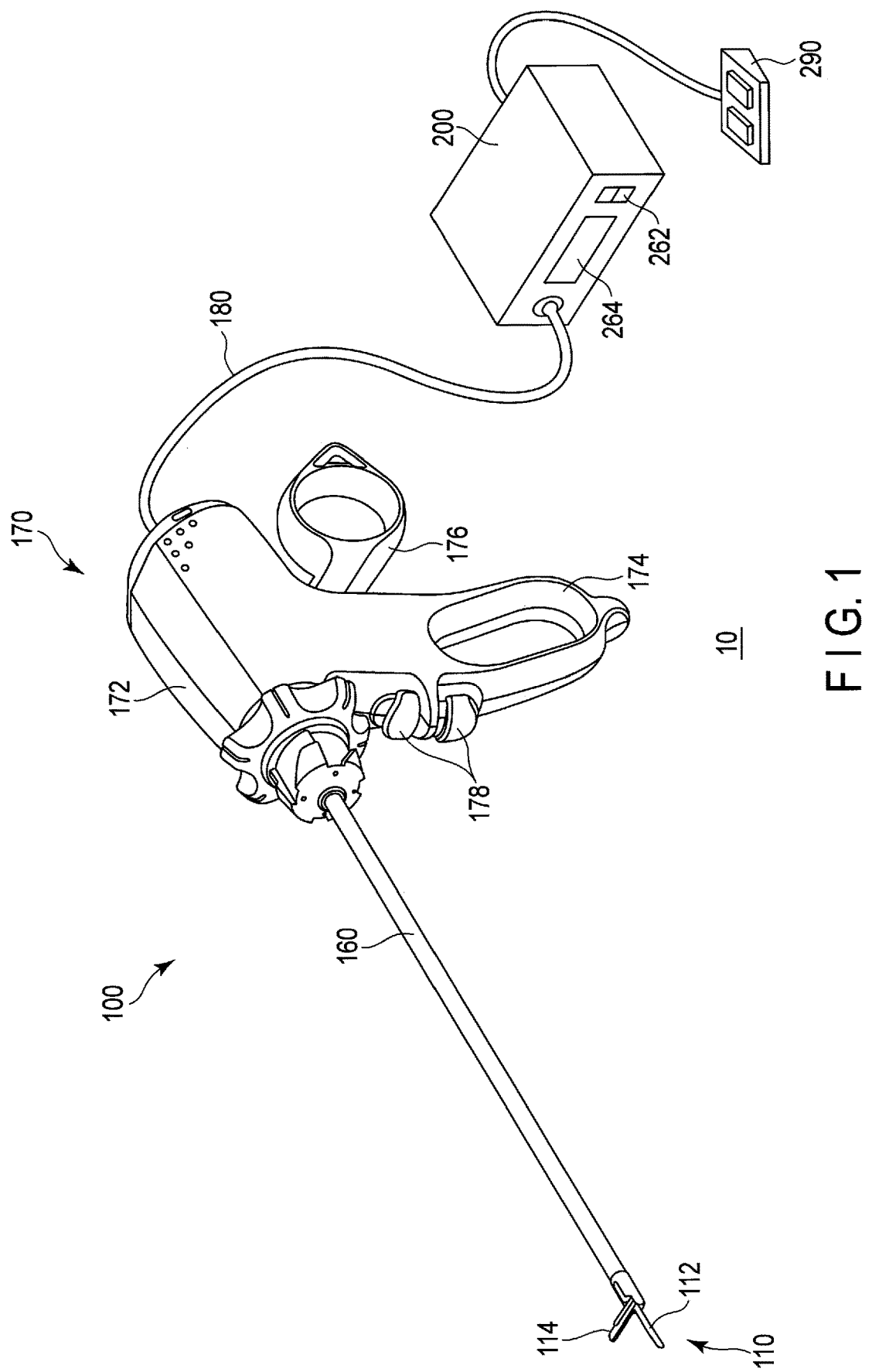
FIG. 1 is a view schematically showing an example of an appearance of a high-frequency treatment system according to an embodiment.

An embodiment will be described with reference to the drawings. A schematic view of a high-frequency treatment system 10 according to the present embodiment is provided in FIG. 1. As shown in this drawing, the high-frequency treatment system 10 includes a high-frequency treatment instrument 100, an electric power source device 200 which supplies electric power to the high-frequency treatment instrument 100, and a foot switch 290.

The high-frequency treatment instrument 100 includes a treating section 110, a shaft 160, and an operation section 170. Hereinafter, for the purpose of description, a side where the treating section 110 is provided will be referred to as a "distal side", and a side where the operation section 170 is provided will be referred to as a "proximal side". The high-frequency treatment system 10 is configured so that the treating section 110 grasps living tissue which is a treatment target such as a blood vessel, for example. The high-frequency treatment system 10 applies a high-frequency voltage to living tissue being grasped, to seal the living tissue.

In the treating section 110 provided in a distal end of the shaft 160, a first grasping member 112 and a second grasping member 114 which form a pair of grasping members are provided. Respective portions of the first grasping member 112 and the second grasping member 114, the portions being brought into contact with living tissue, function as electrodes, respectively. In other words, the first grasping member 112 and the second grasping member 114 function as a bipolar electrode.

In the operation section 170, an operation section main body 172, a fixed handle 174, a movable handle 176, and an output switch 178 are provided. The fixed handle 174 is fixed to the operation section main body 172, and the movable handle 176 is displaced with respect to the operation section main body 172. The movable handle 176 is connected to a wire or a rod which is inserted through the shaft 160. The wire or the rod is connected to the second grasping member 114. Movement of the movable handle 176 is transmitted to the second grasping member 114. The second grasping member 114 is displaced with respect to the first grasping member 112, in accordance with movement of the movable handle 176. As a result, the first grasping member 112 and the second grasping member 114 are opened or closed relative to each other. It is noted that in a certain example, a wire or a rod is connected to both of the first grasping member 112 and the second grasping member 114. In this case, both of the first grasping member 112 and the second grasping member 114 are displaced with respect to the shaft 160, in accordance with movement of the movable handle 176. Then, as a result, the first grasping member 112 and the second grasping member 114 are opened or closed relative to each other.

The output switch 178 includes two buttons, for example. Those buttons are buttons which are pressed when high-frequency electric power is caused to act on living tissue which is a treatment target, by the treating section 110. Upon detection of a press of the buttons, the electric power source device 200 applies a high-frequency voltage across the first grasping member 112 and the second grasping member 114. As a result, living tissue grasped by the treating section 110 is sealed. The high-frequency treatment instrument 100 is configured so that an output level varies depending on which of two buttons is pressed, for example. Also in the foot switch 290, two switches are provided, for example. The two switches of the foot switch 290 have functions which are respectively similar to those of the buttons of the output switch 178. It is noted that either both or one of the output switch 178 and the foot switch 290 may be provided in the high-frequency treatment system 10. Though the following description will be made on the assumption that the output switch 178 is mainly operated, the foot switch 290 may be operated.

On a proximal side in the operation unit 170, one end of a cable 180 is connected. The other end of the cable 180 is connected to the electric power source device 200. The electric power source device 200 controls an operation, such as outputting of energy, of the high-frequency treatment instrument 100, and supplies electric power to the high-frequency treatment instrument 100.

Figure 2:
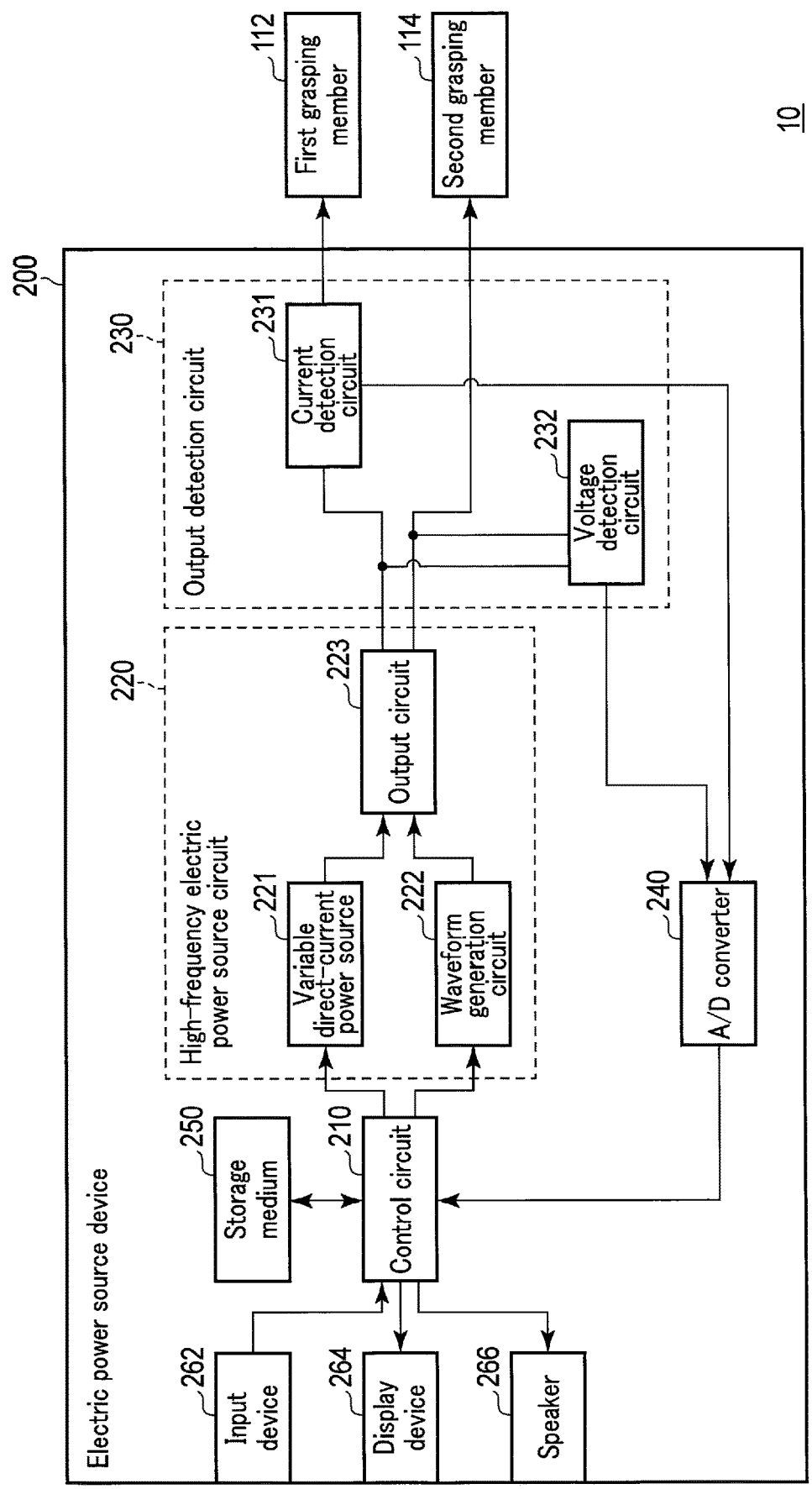
FIG. 2 is a block diagram schematically showing an example of configuration of the high-frequency treatment system according to the embodiment.

FIG. 2 is a block diagram schematically showing an example of configuration of the electric power source device 200. The electric power source device 200 includes a control circuit 210, a high-frequency electric power source circuit 220, an output detection circuit 230, an A/D (analog/digital) converter 240, a storage medium 250, an input device 262, a display device 264, and a speaker 266.

The control circuit 210 includes an integrated circuit (processor) such as central processing unit (CPU), an application specific integrated circuit (ASIC), a field programmable gate array (FPGA), or the like, for example. The control circuit 210 may be formed of an integrated circuit or the like, or may be formed of a combination of a plurality of integrated circuits or the like. The control circuit 210 operates in accordance with a program stored in the control circuit 210 or the storage medium 250, for example. The control circuit 210 acquires information from respective components of the electric power source device 200, and controls operations of the respective components.

The high-frequency electric power source circuit 220 outputs high-frequency electric power which is to be supplied to the high-frequency treatment instrument 100. The high-frequency electric power source circuit 220 includes a variable direct-current electric power source 221, a waveform generation circuit 222, and an output circuit 223. The variable direct-current electric power source 221 outputs direct-current electric power under control of the control circuit 210. An output of the variable direct-current electric power source 221 is transmitted to the output circuit 223. The waveform generation circuit 222 generates an alternating-current waveform and outputs generated alternating-current waveform under control of the control circuit 210. An output of the waveform generation circuit 222 is transmitted to the output circuit 223. The output circuit 223 superposes an output of the variable direct-current electric power source 221 and an output of the waveform generation circuit 222 on each other, and outputs alternating-current electric power. This alternating-current electric power is supplied to the first grasping member 112 and the second grasping member 114 of the high-frequency treatment instrument 100, via the output detection circuit 230.

The output detection circuit 230 includes a current detection circuit 231 and a voltage detection circuit 232. The current detection circuit 231 is interposed at some midpoint in a circuit extending from the high-frequency electric power source circuit 220 to the high-frequency treatment instrument 100, and outputs an analog signal indicating a current value which is output from the high-frequency electric power source circuit 220. The voltage detection circuit 232 outputs an analog signal indicating an output voltage of the high-frequency electric power source circuit 220.

An output signal of the current detection circuit 231 and an output signal of the voltage detection circuit 232 are input to the A/D converter 240. The A/D converter 240 converts an input analog signal into a digital signal, and transmits the digital signal to the control circuit 210. In this manner, the control circuit 210 acquires information about an output voltage and an output current of the high-frequency electric power source circuit 220. Also, the control circuit 210 calculates a value related to impedance of a circuit including the first grasping member 112, living tissue which is a treatment target, and the second grasping member 114, based on the above-described output voltage and output current. That is, the control circuit 210 acquires a value related to impedance of living tissue.

In the storage medium 250, a program used in the control circuit 210, various kinds of parameters, tables, and like used for calculation performed in the control circuit 210 are stored.

The input device 262 includes an input instrument such as a button, a slider, a dial, a keyboard, or a touch panel, for example. The control circuit 210 accepts a user's input to the input device 262. The display device 264 includes a display instrument such as a liquid crystal display, or an LED lamp, for example. The display device 264 shows information concerning the high-frequency treatment system 10 to a user, under control of the control circuit 210. The speaker 266 produces an input sound, an output sound, a warning beep, or the like, for example, under control of the control circuit 210.

[Operations of High-frequency Treatment System]

Operations of the high-frequency treatment system 10 according to the present embodiment will be described. The treating section 110 and the shaft 160 are inserted into an abdominal cavity through an abdominal wall, for example. A user opens and closes the treating section 110 by operating the movable handle 176. Thus, the first grasping member 112 and the second grasping member 114 grasp living tissue which is a treatment target. A user operates the output switch 178 after grasping living tissue with the treating section 110. When the control circuit 210 of the electric power source device 200 detects a press of a button of the output switch 178, the control circuit 210 outputs an instruction concerning drive of the high-frequency electric power source circuit 220.

The high-frequency electric power source circuit 220 applies a high-frequency voltage across the first grasping member 112 and the second grasping member 114 of the treating section 110 under control of the control circuit 210, to cause a high-frequency current to flow through living tissue which is a treatment target. When a high-frequency current flows through living tissue, the living tissue serves as electrical resistance, so that heat is generated in the living tissue and a temperature of the living tissue increases. As a result, protein in the living tissue denatures, so that the living tissue is sealed. By the above-described operations, treatment of living tissue is completed.

Operations of outputting in the electric power source device 200 will be described in detail. Description will be made with reference to a flow chart shown in FIG. 3 which schematically shows actuations of the electric power source device 200 according to the present embodiment. In a step S101, the control circuit 210 judges whether or not the output switch 178 is turned on. If the output switch 178 is not turned on, a return to the step S101 is made in the process. Specifically, the control circuit 210 stands by until the output switch 178 is turned on. When the output switch 178 is turned on, an advance to a step S102 is made in the process. In the step S102, the control circuit 210 exercises first control. Subsequently, in a step S103, the control circuit 210 exercises second control. Subsequently, in a step S104, the control circuit 210 exercises third control. Details of the first control, the second control, and the third control will be provided later. By the above-described processes, output control is finished. As described, in the present embodiment, control is exercised in three stages.

Examples of outputs of the high-frequency treatment system 10 according to the present embodiment and of resistance which is accordingly calculated and is related to living tissue will be described with reference to FIG. 4. In FIG. 4, an abscissa axis represents a time which is measured with a starting time of outputting being set to 0, a left ordinate axis represents output electric power, an output voltage, and an output current, and a right ordinate axis represents resistance serving as a value related to impedance of living tissue. In FIG. 4, a solid line indicates a change in an output voltage, a broken line indicates a change in resistance, a long-dashed single-dotted line indicates a change in an output electric power, and a long-dashed double-dotted line indicates a change in an output current.

As described above, control over an output of the high-frequency treatment system 10 according to the present embodiment is exercised in three stages (three phases). Hence, a period in which electric power is supplied to living tissue includes a first period of a short time in which the first control is exercised immediately after a start of outputting, a second period of approximately one second in which the second control is exercised after the first period, and a third period of approximately two seconds in which the third control is exercised after the second period. An output provided by the first control will be referred to as a "first output", an output provided by the second control will be referred to as a "second output", and an output provided by the third control will be referred to as a "third output".

In the first control, high-frequency electric power having a predetermined electric-power value is supplied to living tissue for a predetermined period. This first period is approximately 100 milliseconds, for example. For the first period, a value related to impedance is acquired. A value related to impedance which is acquired at that time varies depending on a size, a kind, a condition, or the like of living tissue which is a treatment target. Hence, in the present embodiment, a condition of living tissue which is a treatment target is comprehended based on a value related to impedance which is acquired in the first period in which the first control is exercised, and a control parameter used for later control is determined. That is, a control parameter commensurate with a property of living tissue which is a treatment target is set. Also, in the first control, predetermined electric power which is not so great is supplied to living tissue, so that overshoot of an output is suppressed.

In the second control, a voltage which linearly increases is applied to living tissue. In the second period in which the second control is exercised, a temperature of living tissue increases. The second control is exercised until it is detected that a value related to impedance being measured becomes a minimum. When a value related to impedance being measured becomes a minimum, control is switched to the third control. In the second control, as moisture evaporates, a temperature increases afterward, so that a value related to impedance correspondingly increases.

In the third control, control which produces constant electric power as an output or control which produces a constant voltage as an output is exercised. When a value related to impedance and an elapsed time from a start of the third control satisfy a predetermined requirement, the third control is finished.

Below, the first to third control will be described in detail.

[With Regard to First Control]

Figure 5:
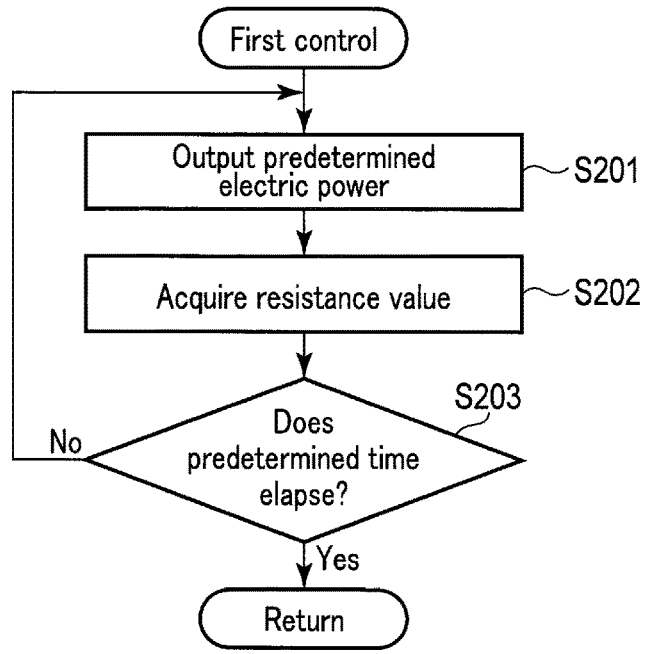
FIG. 5 is a flow chart showing an example of first control in the high-frequency treatment system according to the embodiment.

The first control will be described with reference to a flow chart shown in FIG. 5.

In a step S201, the control circuit 210 causes the high-frequency electric power source circuit 220 to supply alternating-current electric power having a predetermined electric-power value to living tissue which is a treatment target grasped by the first grasping member 112 and the second grasping member 114. As a result of the supply of alternating-current electric power, an alternating current flows through living tissue.

In a step S202, the control circuit 210 acquires a value related to impedance of living tissue which is a treatment target. For example, the control circuit 210 acquires a current detected by the current detection circuit 231 of the output detection circuit 230 and a voltage detected by the voltage detection circuit 232, and calculates a value related to impedance based on those values being acquired. In this regard, a value related to impedance, the value being calculated, may be any of various values related to impedance, such as an absolute value of impedance which is a complex number, or a resistance value which is a real component of impedance, for example. Also, admittance which is a reciprocal of impedance may be used. Though the following description will be made by taking a case where a resistance value is used as a value related to impedance, as an example, the same holds true for also cases where other values related to impedance are used.

In a step S203, the control circuit 210 judges whether or not a predetermined time elapses. It is noted that a predetermined time is 100 milliseconds, for example. If a predetermined time does not elapse, a return to the step S201 is made in the process. Specifically, supply of predetermined electric power and acquisition of a resistance value are repeated. When a predetermined time elapses, the first control is finished, and switching to the second control is performed.

It is noted that a resistance value which is acquired in the first control will be referred to as an initial resistance value R0. An initial resistance value may be a resistance value that is acquired for the first time, or a resistance value which is acquired in any of time intervals included in the first period in which the first control is exercised, or may be an average value, an intermediate value, or the like of resistance values which are acquired in any of time intervals included in the first period.

[With Regard to Second Control]

The second control will be described in detail. The second control is control which is optimized in order to stably seal a blood vessel or the like.

In the present embodiment, the control circuit 210 controls an output voltage V(t) applied to living tissue in the second control so that it follows a desired control trajectory represented by the following expression (1).

$$V(t)=(V(Z)/GV) \times t \tag{1}$$

It is noted that t represents a time which elapses from a start of treatment, that is, a time which elapses from a start of the first control. Meanwhile, t may represent a time which elapses from a start of the second control. V(Z) represents a constant such as a maximum value of an output voltage, for example. GV represents a gradient value. Thus, (V(Z)/GV) represents a value of rise in an output voltage per unit time, that is, a gradient (rate of increase).

GV is determined based on an initial resistance value which is acquired in the first control. GV is determined by the following expression (2), based on the initial resistance value R0, for example.

$$GV = a \cdot R0 + b \tag{2}$$

It is noted that a and b are constants. Also, a and b are values which are empirically adjusted so that a resistance value becomes a minimum in approximately one second when the output voltage V(t) is applied to living tissue.

Additionally, the above-described expression (2) is not limited to a linear function, and may be another expression such as a higher-degree function. However, it is preferable that the expression (2) is a linear function, rather than a higher-degree function, in order that the initial resistance value R0 does not too significantly affect the above-described expression (1). Further, also the above-described expression (1) is a linear function of a time. To be a linear function enhances stability and allows a temperature to increase to an appropriate degree. Since an output voltage is a linear function of a time, electric power applied to living tissue quadratically increases with time. It is noted that offset may be given to the output voltage V(t). Specifically, the above-described expression (1) may be transformed into the following expression where c represents a constant.

$$V(t)=(V(Z)/GV) \times t + c \tag{3}$$

According to the above-described expressions (1) and (2), the initial resistance value R0 is relatively high in a small blood vessel, for example, and so (V(Z)/GV) representing a gradient is relatively gentle. Specifically, in a thin blood vessel, an output voltage increases relatively slowly, and therefore, applied electric power increases relatively slowly. On the other hand, the initial resistance value R0 is relatively low in a large blood vessel, for example, and so (V(Z)/GV) representing a gradient is relatively steep. Specifically, in a thick blood vessel, an output voltage increases relatively fast, and therefore, applied electric power increases relatively fast.

The gradient (V(Z)/GV) may be calculated on each occasion based on a relationship above-described in expressions (1) and (2) and the initial resistance value R0, to be used, or may be determined based on a table which shows a relationship between the initial resistance value R0 and the gradient (V(Z)/GV), and which is previously stored in the storage medium 250, and based on the initial resistance value R0 being acquired.

Figure 6:
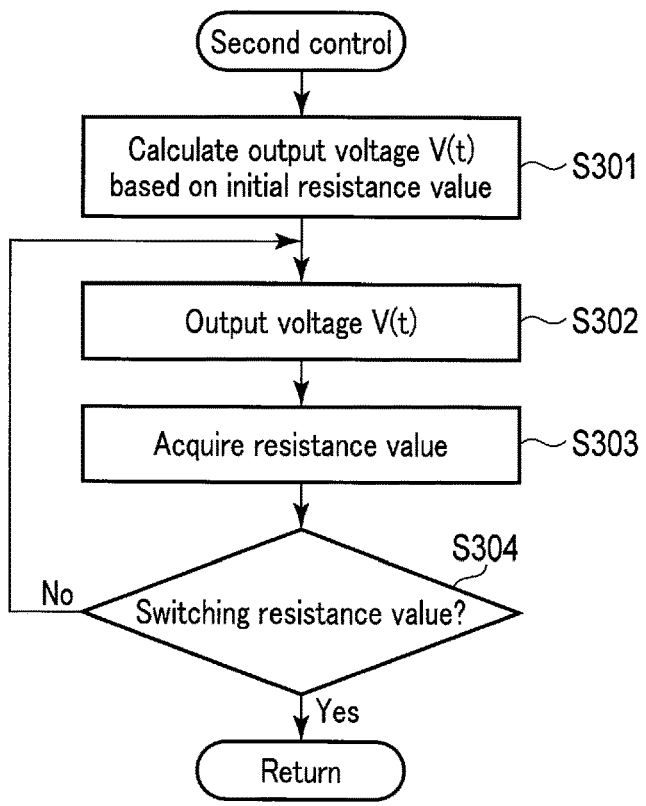
FIG. 6 is a flow chart showing an example of second control in the high-frequency treatment system according to the embodiment.

Operations of the electric power source device 200 in the second control will be described with reference to a flow chart shown in FIG. 6.

In a step S301, the control circuit 210 calculates a relationship between a time and the output voltage V(t), as a desired control trajectory, based on the initial resistance value R0. The output voltage V(t) is determined using the above-described expressions (1) and (2), for example.

In a step S302, the control circuit 210 causes the high-frequency electric power source circuit 220 to output the voltage V(t) being in correspondence with a time. In a step S303, the control circuit 210 acquires a resistance value of living tissue.

In a step S304, the control circuit 210 judges whether or not the resistance value which is acquired in the step S303 is a switching resistance value. It is noted that a switching resistance value is a resistance value which is a requirement for finishing the second control. A switching resistance value can be a value which is provided when a resistance value, a change of which is measured, becomes a minimum. In order to facilitate detection of a minimum value, a value provided when a resistance value increases by a predetermined amount after becoming a minimum may be employed as a switching resistance value. Specifically, in a step S304, it may be determined that a resistance value becomes available as a switching resistance value when a resistance value increases by a predetermined amount after the resistance value decreases to become a locally minimum. If it is determined that a resistance value is not a switching resistance value in the step S304, a return to the step S302 is made in the process, and the above-described processes are repeated. On the other hand, if it is determined that a resistance value is a switching resistance value, the second control is finished and switching to the third control is performed.

By the above-described control, an output voltage and a resistance value are as shown in FIG. 4. Specifically, in the second period in which the second control is exercised, an output voltage linearly increases. At that time, output electric power quadratically increases. A resistance value which is acquired in the second period decreases slowly with passage of time. In an example shown in FIG. 4, at a spot where a resistance value slightly increases after becoming a locally minimum, the second control is finished. When the second control is finished, the third control which will be later described is started. A time point at which switching from the second control to the third control is performed will be referred to as a control switching time point.

It is noted that although the example in which an output voltage is controlled has been described here, either an output current or output electric power may be controlled in the same manner so that it linearly increases.

A time taken for a resistance value to become a minimum is set to a relatively long time of approximately one second, so that a temperature of living tissue can be made uniform while a time for treatment is shortened. Also, a time taken for a resistance value to become a minimum is kept constant at approximately one second, regardless of a size or the like of a treatment target, so that variation in results of respective treatments can be suppressed. It is noted that in a case where the same energy is applied, the smaller a blood vessel is, the shorter a time taken for a resistance value to become a locally minimum is.

[With Regard to Third Control]

The third control will be described in detail. In the third control, control is exercised so that constant electric power or a constant voltage which is determined by a later-described predetermined method is produced as an output. Also, in the present embodiment, a terminate resistance value which is a resistance value provided when outputting is stopped is determined. In the present embodiment, the third control is exercised until a predetermined minimum output time elapses and a resistance value reaches a terminate resistance value.

Figure 7:
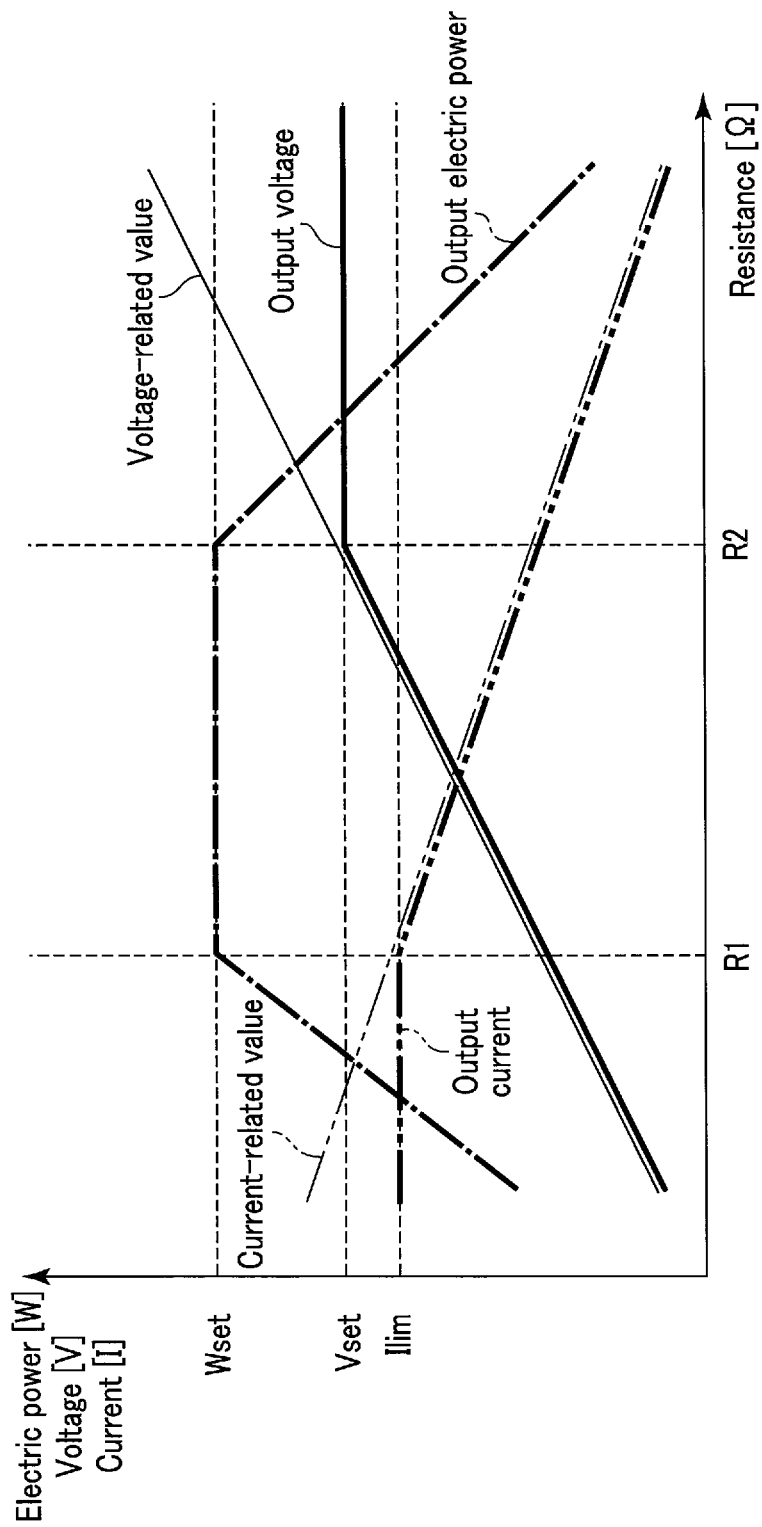
FIG. 7 is a view for explaining an example of an output characteristic in third control of an electric power source device according to the embodiment.

FIG. 7 shows an example of an output characteristic in the third control of the electric power source device 200 according to the present embodiment. In the third control, the set electric-power value Wset is set based on parameters related to the first control and the second control. In the third control, constant-electric-power control in which the set electric-power value Wset is produced as an output is exercised, to the extent possible. During a period of the third control, resistance of living tissue which is a treatment target is changed. Generally, resistance shows a tendency to increase as treatment proceeds.

In the present embodiment, a relationship between a voltage value and a current value, which produces the set electric-power value Wset, is previously prepared. Here, a voltage value and a current value which are in the previously-prepared relationship will be referred to as a voltage-related value and a current-related value, respectively. In FIG. 7, an example of a voltage-related value is indicated by a thin solid line, and an example of a current-related value is indicated by a thin long-dashed double-dotted line. As shown in this drawing, in order to apply predetermined electric power to living tissue, a voltage which is to be applied to living tissue is caused to increase in accordance with increase of resistance. Also, adjustment is made so that electric power which is applied when a voltage being applied increases is constant, and so, a current flowing through living tissue decreases as resistance increases.

Further, in the present embodiment, in the third control, the set voltage value Vset is set based on parameters related to the first control and the second control. The set voltage value Vset functions as a limit value of an output voltage. Accordingly, an output voltage is output so as to be changed in such a manner as indicated by a thick solid line in FIG. 7, in accordance with a change of resistance. Specifically, when a resistance value is lower than a second value R2, a voltage following a voltage-related value is output, and when a resistance value is equal to or higher than the second value R2, a voltage of the set voltage value Vset is output. At that time, also a current flowing through living tissue decreases as resistance of living tissue increases. Thus, electric power applied to living tissue decreases as resistance increases.

Likewise, a limit value Ilim of an output current is previously set, and an output current is output so as to be changed in such a manner as indicated by a thick long-dashed double-dotted line in FIG. 7 in accordance with a change of resistance. Specifically, when a resistance value is higher than a first value R1, a current following a current-related value is output, and when a resistance value is equal to or lower than the first value R1, a current of the limit value Ilim is output. In order that a current value is constant even though a resistance value is changed, an output voltage shows a tendency to decrease as resistance decreases.

As a result, as indicated by a long-dashed single-dotted line in FIG. 7, constant-electric-power control is exercised over output electric power so that output electric power becomes constant at a set electric-power value as indicated by a long-dashed single-dotted line when a resistance value is higher than the first value R1 and is lower than the second value R2. On the other hand, when a resistance value becomes equal to or higher than the second value R2, output electric power decreases as resistance increases because an output voltage does not increase. That is, constant-voltage control is exercised so that an output voltage is equal to the set voltage value Vset.

Additionally, it is generally supposed that resistance of living tissue has a value close to the second value R2 or the like when switching from the second control to the third control is performed.

In the third control, the set electric-power value Wset and the set voltage value Vset are determined based on parameters related to the first control and the second control. The parameters related to the first control and the second control can show a condition of living tissue before the third control is started. Then, in the present embodiment, the optimum set electric-power value Wset and the optimum set voltage value Vset are set using those parameters.

<With Regard to Setting of Output Electric Power in Third Control>

Some examples of a method for setting the set electric-power value Wset will be described. The set electric-power value Wset is set by any of the following methods, for example. The set electric-power value Wset can be set to any of values of approximately 5 W to 200 W, for example, though the set electric-power value Wset is not limited to the foregoing values.

First Example

In a first example, the set electric-power value Wset is set to a maximum value Wmax2 of output electric power in the second control.

Second Example

In a second example, the set electric-power value Wset is set based on a maximum value of output electric power in the second control. For example, the set electric-power value Wset is calculated by Wset=f(Wmax2) using the maximum value Wmax2 of output electric power in the second control and a predetermined function f(x). For example, the set electric-power value Wset may be set to a value equal to 90% or the like of a maximum value of electric power in the second control. A relationship between the maximum value Wmax2 of output electric power in the second control and the set electric-power value Wset may be stored in a table.

Third Example

In a third example, the set electric-power value Wset is set based on an output electric-power value Wend2 which is provided when the second control is finished. For example, the set electric-power value Wset is calculated by Wset=f(Wend2) using the output electric-power value Wend2 which is provided when the second control is finished, and the predetermined function f(x). For example, the set electric-power value Wset may be set to an output electric-power value which is provided when the second control is finished, or may be set to a value equal to 90% or the like of an electric-power value which is provided when the second control is finished. A relationship between the output electric-power value Wend2 which is provided when the second control is finished and the set electric-power value Wset may be stored in a table.

Fourth Example

In a fourth example, the set electric-power value Wset is calculated as a function of the initial resistance value R0 and a duration Dt of the second control. The duration Dt is acquired when the second control is finished. The set electric-power value Wset may be calculated by substitution of the initial resistance value R0 and the duration Dt of the second control into a predetermined function, or may be obtained by reference to a table on which the set electric-power value Wset being in correspondence with the initial resistance value R0 and the duration Dt of the second control is recorded.

An example of a table showing a relationship of the set electric-power value Wset relative to the initial resistance value R0 and the duration Dt of the second control is shown in FIG. 8. As shown in this drawing, values (a to l) for Wset are provided so as to correspond to values for the initial resistance value R0 (R0_1 to R0_4) and values for the duration Dt (Dt_1 to Dt_3). Values a to l each as the set electric-power value Wset may be different from each other, or some of those values may be identical to each other. For example, the higher a value as the initial resistance value R0 is, the lower the set electric-power value Wset is. In other words, in a case where a treatment target is a blood vessel, the smaller a blood vessel is, the higher the initial resistance value R0 is, and so, the set electric-power value Wset is low. Also, for example, the longer the duration Dt is, the higher the set electric-power value Wset is.

Fifth Example

In a fifth example, the set electric-power value Wset is calculated as a function of the initial resistance value R0. The set electric-power value Wset may be calculated using a function, or may be obtained by reference to a table like that shown in FIG. 9, for example.

Sixth Example

In a sixth example, the set electric-power value Wset is calculated as a function of the duration Dt of the second control. The set electric-power value Wset may be calculated using a function, or may be obtained by reference to a table like that shown in FIG. 10, for example.

<With Regard to Setting of Output Voltage in Third Control>

Some examples of a method for setting the set voltage value Vset will be described. The set voltage value Vset is set by any of the following methods, for example. The set voltage value Vset can be set to any of values of approximately 15 V to 200 V, for example, though the set voltage value Vset is not limited to the foregoing values.

First Example

In a first example, the set voltage value Vset is set based on an output voltage value which is provided when the second control is finished. For example, the set voltage value Vset is set to an output voltage value which is provided when the second control is finished, is set to a value equal to 90% or the like of the foregoing output voltage value, or is set to a value which is obtained by substitution of the foregoing output voltage value into a predetermined function.

Second Example

In a second example, the set voltage value Vset is calculated as a function of the initial resistance value R0 and the duration Dt of the second control. The duration Dt is acquired when the second control is finished. The set voltage value Vset may be calculated by substitution of the initial resistance value R0 and the duration Dt of the second control into a predetermined function, or may be obtained by reference to a table, like the table shown in FIG. 8, for example, on which the set voltage value Vset being in correspondence with the initial resistance value R0 and the duration Dt of the second control is recorded. For example, the higher the initial resistance value R0 is, the lower the set voltage value Vset is. In other words, in a case where a treatment target is a blood vessel, the smaller a blood vessel is, the higher the initial resistance value R0 is, and so, the set voltage value Vset is low. Also, for example, the longer the duration Dt is, the higher the set voltage value Vset is.

Third Example

In a third example, the set voltage value Vset is calculated as a function of the initial resistance value R0. The set voltage value Vset may be calculated using a function, or may be obtained by reference to a table like the table shown in FIG. 9, for example.

Fourth Example

In a fourth example, the set voltage value Vset is calculated as a function of the duration Dt of the second control. The set voltage value Vset may be calculated using a function, or may be obtained by reference to a table like the table shown in FIG. 10, for example.

<With Regard to Setting of Terminate Resistance Value in Third Control>

A method for setting a terminate resistance value which is provided when outputting is stopped in the third control will be described. Though a case where a resistance value is used will be described here, the same holds true for also cases where values related to impedance, other than a resistance value, are used. The terminate resistance value Rstop which is a resistance value provided when outputting is stopped is obtained by the following expression (4), for example.

$$Rstop = Rin + Radd \quad (4)$$

It is noted that Rin represents a resistance value which is related to living tissue and is acquired at a starting time of the third control. In other words, Rin represents a resistance value corresponding to the above-described switching resistance value. Additionally, Rin may be minimum resistance measured in the second control. Also, as Rin, the initial resistance value R0 acquired in the first control may be used.

Further, Radd represents an added resistance which is determined based on an initial condition of living tissue. Some examples of a method for setting an added resistance value Radd will be described.

First Example

The added resistance value Radd is calculated as a function of the initial resistance value R0. For example, a table, like the table shown in FIG. 9, which shows a relationship between the initial resistance value R0 and the added resistance value Radd is stored in the storage medium 250, and the added resistance value Radd is set based on the table and the initial resistance value R0 which is measured in the first control. It is noted that the higher the initial resistance value R0 is, the lower the added resistance value Radd is. In other words, in a case where a treatment target is a blood vessel, the smaller a blood vessel is, the higher the initial resistance value R0 is, and so, the added resistance value Radd is low.

Second Example

The added resistance value Radd is calculated as a function of the initial resistance value R0 and the duration Dt of the second control. For example, a table, like the table shown in FIG. 8, which shows a relationship of the added resistance value Radd relative to the initial resistance value R0 and the duration Dt is stored in the storage medium 250, and the added resistance value Radd is set based on the initial resistance value R0 and the duration Dt which are measured, together with the foregoing table. It is noted that the higher the initial resistance value R0 is, the lower the added resistance value Radd is. Also, the longer the duration is, the higher the added resistance value Radd is. The added resistance value Radd is set based on the initial resistance value R0 and the duration Dt of the second control, so that the added resistance value Radd is more appropriately set than that in a case where the added resistance value Radd is set based on only the initial resistance value R0.

Third Example

The added resistance value Radd may be selected in accordance with an output level as is set. For example, the higher an output level is, the higher the added resistance value Radd is, and the lower an output level is, the lower the added resistance value Radd is. The added resistance value Radd is set using an output level, together with the initial resistance value R0 or the duration Dt of the second control, so that a more appropriate value can be set.

In all of the above-described first to third examples, the smaller a blood vessel, for example, is, the lower the added resistance value Radd is, and the larger a blood vessel is, the higher the added resistance value Radd is. It is noted that the terminate resistance value Rstop is higher than the initial resistance value R0.

As described above, because of use of the initial resistance value R0 or the like which varies with a treatment target such as a gauge of a blood vessel, for example, the terminate resistance value Rstop commensurate with a treatment target is appropriately set. By exercising output control using the stop resistance value Rstop which is set in the above-described manner, it is possible to provide suitable treatment.

Likewise, also a minimum output time Tmin is previously prepared in a form of a relationship to the initial resistance value R0 and the duration Dt, and the minimum output time Tmin may be set based on the initial resistance value R0 and the duration Dt, together with the foregoing relationship.

As described above, for example, relationships of various parameters relative to the initial resistance value R0 and the duration Dt may be previously determined, and stored in the storage medium 250. That is, a table showing the relationships is as shown in FIG. 11, for example.

<With Regard to Operations in Third Control>

Figure 12:
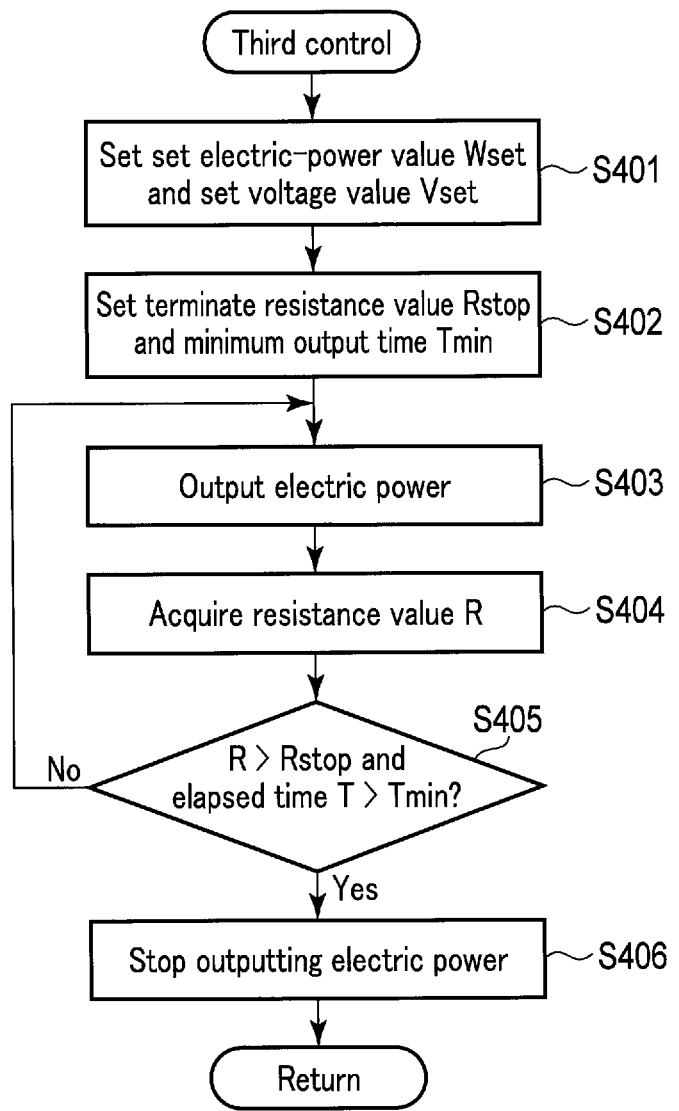
FIG. 12 is a flow chart showing an example of the third control in the high-frequency treatment system according to the embodiment.

Operations of the electric power source device 200 in the third control will be described with reference to a flow chart shown in FIG. 12.

In a step S401, the control circuit 210 sets the set electric-power value Wset and the set voltage value Vset based on parameters related to the first control and the second control. Any method in the above-described examples may be used as a method for setting the set electric-power value Wset and the set voltage value Vset.

In a step S402, the control circuit 210 sets the added resistance value Radd and sets the terminate resistance value Rstop based on parameters related to the first control and the second control. Any method in the above-described examples may be used as a method for setting the terminate resistance value Rstop. Also, the control circuit 210 sets the minimum output time Tmin.

In a step S403, the control circuit 210 causes the high-frequency electric power source circuit 220 to output electric power based on setting for outputting. In a step S404, the control circuit 210 acquires the resistance value R using a value detected in the output detection circuit 230. In a step S405, the control circuit 210 judges whether or not a requirement for stop is satisfied, in other words, whether or not the resistance value R as measured is higher than the terminate resistance value Rstop, and whether or not an elapsed time T is longer than the minimum output time Tmin. In a case where the resistance value R as measured is equal to or lower than the terminate resistance value Rstop, or the elapsed time T is equal to or shorter than the minimum output time Tmin, a return to the step S403 is made in the process.

In judgment in the step S405, if it is judged that the resistance value R as measured is higher than the terminate resistance value Rstop and the elapsed time T is longer than the minimum output time Tmin, an advance to a step S406 is made in the process. In the step S406, the control circuit 210 causes the high-frequency electric power source circuit 220 to stop outputting. Thereafter, the third control is finished. By the above-described processes, supply of high-frequency electric power from the electric power source device 200 to the high-frequency treatment instrument 100 is finished. It is noted that in the step S406, an output from the high-frequency electric power source circuit 220 may be lowered to such a degree that living tissue does not denature due to a high-frequency current, instead of causing the high-frequency electric power source circuit 220 to stop outputting. In this case, the high-frequency electric power source circuit 220 is caused to stop outputting based on passage of a predetermined time since lowering of an output, or based on an operation by an operator or the like.

[Features of High-frequency Treatment System]

With the high-frequency treatment system 10 according to the present embodiment, a set output value in the third control is set based on information related to the first control or the second control. Accordingly, optimum energy can be applied to living tissue without a shortage of energy being supplied to living tissue which is a treatment target, or without supply of excessive energy to living tissue.

[Modification]

Figure 13:
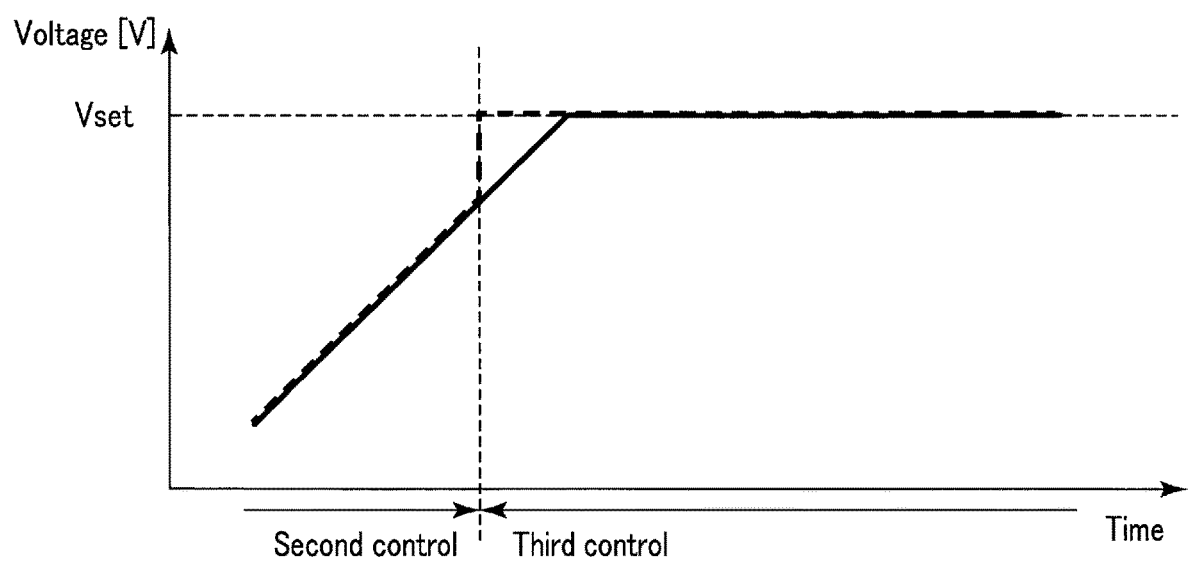
FIG. 13 is a view for explaining voltage control which is exercised when switching from the second control to the third control is performed.

A modification of the above-described embodiment will be described. FIG. 13 is a view showing a change in a voltage value with time in a case where constant-voltage control is exercised when switching from the second control to the third control is performed. An example shown by a broken line in FIG. 13 is an example of an output in a case where an output voltage gradually increases with passage of time in the second control and is switched to the set voltage value Vset at a moment when switching to the third control is performed. At that moment when switching from the second control to the third control is performed, an output voltage is abruptly changed. Such an abrupt change may probably make control unstable.

In view of this, in the present modification, as shown by a solid line in FIG. 13, a gradient of an increase in voltage in the second control is maintained until an output voltage reaches the set voltage value Vset. After an output voltage reaches the set voltage value Vset, an output voltage is kept equal to the set voltage value Vset. It is noted that it is unnecessary to change a starting point of measurement of elapsed time also in this case.

By controlling a change in voltage in the above-described manner, it is possible to prevent control from becoming unstable due to an abrupt change in voltage.

Additional advantages and modifications will readily occur to those skilled in the art. Therefore, the embodiments in their broader aspects are not limited to the specific details and representative embodiments shown and described herein. Accordingly, various modifications may be made without departing from the spirit or scope of the general inventive concept as defined by the appended claims and their equivalents.

What is claimed is:

1. An electric power source device configured to control a power output to a treatment instrument that treats living tissue with a high-frequency current, the electric power source device comprising:
at least one processor configured to:
detect a value related to an initial impedance of the living tissue;
determine a control switching time point upon determining that a value related to the impedance of the living tissue is a minimum value;
set a desired control trajectory of an output voltage, in which the output voltage increases with time, based on the initial impedance of the living tissue;
control the power output to the treatment instrument for a period of time until reaching the control switching time point based on the detected value related to the initial impedance;
set a set electric-power value of the power output based on a parameter related to the control over the output before the control switching time point, the set electric-power value being an upper limit of the power output and the set voltage value being an upper limit of the output voltage;
perform constant-electric-power control by controlling the power output to the treatment instrument based on the set electric-power value starting at the control switching time point; and
in response to performing the constant-electric-power control to maintain the constant set electric-power value until a voltage value of the output voltage becomes equal to or greater than the set voltage value that is set based on at least one of (i) the initial impedance, (ii) an output voltage value at the control switching time point, and (iii) an output time before the control switching time point, perform a constant-voltage control by controlling the power output to maintain the voltage value of the power output at the set voltage value.

2. The electric power source device according to claim 1, wherein the processor is configured to set the set electric-power value based on a maximum value of electric power related to the power output before reaching the control switching time point.

3. The electric power source device according to claim 1, wherein the processor is configured to set the set electric-power value based on an electric-power value of the power output immediately before the control switching time point.

4. The electric power source device according to claim 1, wherein the processor is configured to:

set a requirement to stop the power output at and after the control switching time point based on the parameter related to the control of the power output before reaching the control switching time point; and control the power output at and after the control switching time point using the set voltage value, and stop the power output when the requirement to stop the power output is satisfied.

5. The electric power source device according to claim 4, wherein the requirement to stop the power output includes at least one of a value related to the impedance of the living tissue and a value related to a time of the power output.

6. The electric power source device according to claim 1, wherein the processor is configured to use the value related to the initial impedance as the parameter.

7. The electric power source device according to claim 1, wherein the processor is configured to use a value related to a length of a time period before the control switching time point as the parameter.

8. The electric power source device according to claim 1, wherein the processor is configured to increase the voltage value of the power output at a constant rate before the control switching time point.

9. The electric power source device according to claim 1, wherein the processor is configured to set the set voltage value based on the output voltage value at the control switching time point.

10. The electric power source device according to claim 1, wherein the processor is configured to set the set voltage value as a function of the initial impedance and a power output time before the control switching time point.

11. The electric power source device according to claim 1, wherein the processor is configured to set the set voltage value as a function of the initial impedance, or the processor is configured to calculate the set voltage value using the function of the initial impedance.

12. The electric power source device according to claim 1, wherein the processor is configured to set the set voltage value as a function of an output time before the control switching time point, or the processor is configured to calculate the set voltage value using the function of the output time before the control switching time point.

13. A high-frequency treatment system comprising:
the electric power source device according to claim 1; and
the treatment instrument.

14. An actuating method of an electric power source device, the electric power source device being configured to control a power output to a treatment instrument that treats living tissue with a high-frequency current, the method comprising:

detecting a value related to an initial impedance of the living tissue;

determining a control switching time point upon determining that a value related to the impedance of the living tissue is a minimum value;

setting a desired control trajectory of an output voltage, in which the output voltage increases with time, based on the initial impedance of the living tissue;

controlling the power output to the treatment instrument for a period of time until reaching the control switching time point based on the detected value related to the initial impedance;

setting a set electric-power value of the power output based on a parameter related to the control over the output before the control switching time point, the set electric-power value being an upper limit of the power output and the set voltage value being an upper limit of the output voltage;

performing a constant-electric-power control by controlling the power output to the treatment instrument based on the set electric-power value starting at the control switching time point; and in response to performing the constant-electric-power control to maintain the constant set electric-power value until a voltage value of the output voltage becomes equal to or greater than the set voltage value that is set based on at least one of (i) the initial impedance, (ii) an output voltage value at the control switching time point, and (iii) an output time before the control switching time point, performing a constant-voltage control by controlling the power output to maintain the voltage value of the power output at the set voltage value.

* * * * *